(12) United States Patent
Knapp et al.

(10) Patent No.: US 11,344,300 B2
(45) Date of Patent: May 31, 2022

(54) SPECIMEN CAPTURE STAPLER

(71) Applicant: Covidien LP, Mansfield, MA (US)

(72) Inventors: Robert Knapp, Middlebury, CT (US); Matthew Eschbach, Cheshire, CT (US)

(73) Assignee: Covidien LP, Mansfield, MA (US)

(*) Notice: Subject to any disclaimer, the term of this patent is extended or adjusted under 35 U.S.C. 154(b) by 289 days.

(21) Appl. No.: 16/792,957

(22) Filed: Feb. 18, 2020

(65) Prior Publication Data
US 2020/0305866 A1 Oct. 1, 2020

Related U.S. Application Data

(60) Provisional application No. 62/824,106, filed on Mar. 26, 2019.

(51) Int. Cl.
*A61B 17/072* (2006.01)
*A61B 17/00* (2006.01)
(Continued)

(52) U.S. Cl.
CPC ...... *A61B 17/072* (2013.01); *A61B 17/00234* (2013.01); *A61B 17/07207* (2013.01);
(Continued)

(58) Field of Classification Search
CPC ............... A61B 17/068; A61B 17/072; A61B 17/07207; A61B 17/115; A61B 17/00234;
(Continued)

(56) References Cited

U.S. PATENT DOCUMENTS 30,471 A 10/1860 Dudley
35,164 A 5/1862 Logan et al.
(Continued)

FOREIGN PATENT DOCUMENTS

DE 25796 C 1/1884
DE 3542667 A1 6/1986
(Continued)

OTHER PUBLICATIONS

Extended European Search Report issued in corresponding Appl. No. EP 20165597.4 dated Aug. 5, 2020 (7 pages).
(Continued)

*Primary Examiner* — Scott A Smith
(74) *Attorney, Agent, or Firm* — Carter, DeLuca & Farrell LLP

(57) ABSTRACT

A surgical stapling device includes an end effector and a handle assembly operably coupled to the end effector. The end effector includes an anvil assembly and a cartridge assembly. The surgical stapling device also includes a specimen bag adhered to both the anvil assembly and the elongated support channel of the cartridge assembly. The specimen bag includes a drawstring within a drawstring housing. Once the surgical stapling device is inserted into a patient's body and the anvil assembly and the cartridge assembly are open, a tissue specimen is placed into the specimen bag. The anvil assembly and the cartridge assembly are then closed on the tissue specimen and the surgical stapling device is fired. The specimen bag then separates from the surgical stapling device and both the surgical stapling device and the specimen bag are removed from the patient.

10 Claims, 7 Drawing Sheets

(51) Int. Cl.
*A61B 17/221* (2006.01)
*A61B 17/295* (2006.01)
*A61B 17/068* (2006.01)

(52) U.S. Cl.
CPC .......... *A61B 17/068* (2013.01); *A61B 17/221* (2013.01); *A61B 17/295* (2013.01); *A61B 2017/00287* (2013.01); *A61B 2017/07214* (2013.01); *A61B 2017/07257* (2013.01); *A61B 2017/07271* (2013.01)

(58) Field of Classification Search
CPC ....... A61B 17/22; A61B 17/221; A61B 17/29; A61B 17/295; A61B 2017/00287; A61B 2017/07214; A61B 2017/07228
USPC ..... 227/19, 175.1, 176.1, 180.1; 606/1, 109, 606/114, 139, 167, 170, 205, 219
See application file for complete search history.

(56) References Cited

U.S. PATENT DOCUMENTS

| | | |
|---|---|---|
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,396 A | 7/1998 | Mastri et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,865,361 A | 2/1999 | Milliman et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,241,139 B1 * | 6/2001 | Milliman ......... A61B 17/07207 227/175.1 |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |

(56) References Cited

U.S. PATENT DOCUMENTS

| | | | |
|---|---|---|---|
| 6,994,696 | B2 | 2/2006 | Suga |
| 7,014,648 | B2 | 3/2006 | Ambrisco et al. |
| 7,018,373 | B2 | 3/2006 | Suzuki |
| 7,052,454 | B2 | 5/2006 | Taylor |
| 7,052,501 | B2 | 5/2006 | McGuckin, Jr. |
| 7,090,637 | B2 | 8/2006 | Danitz et al. |
| 7,115,125 | B2 | 10/2006 | Nakao et al. |
| 7,235,089 | B1 * | 6/2007 | McGuckin, Jr. ............... A61B 17/07207 606/167 |
| 7,270,663 | B2 | 9/2007 | Nakao |
| 7,273,488 | B2 | 9/2007 | Nakamura et al. |
| 7,410,491 | B2 | 8/2008 | Hopkins et al. |
| 7,547,310 | B2 | 6/2009 | Whitfield |
| 7,618,437 | B2 | 11/2009 | Nakao |
| 7,670,346 | B2 | 3/2010 | Whitfield |
| 7,722,626 | B2 | 5/2010 | Middleman et al. |
| 7,762,959 | B2 | 7/2010 | Bilsbury |
| 7,785,251 | B2 | 8/2010 | Wilk |
| 7,819,121 | B2 | 10/2010 | Amer |
| 7,837,612 | B2 | 11/2010 | Gill et al. |
| RE42,050 | E | 1/2011 | Richard |
| 7,892,242 | B2 | 2/2011 | Goldstein |
| 8,016,771 | B2 | 9/2011 | Orban, III |
| 8,057,485 | B2 | 11/2011 | Hollis et al. |
| 8,075,567 | B2 | 12/2011 | Taylor et al. |
| 8,097,001 | B2 | 1/2012 | Nakao |
| 8,152,820 | B2 | 4/2012 | Mohamed et al. |
| 8,172,772 | B2 | 5/2012 | Zwolinski et al. |
| 8,206,401 | B2 | 6/2012 | Nakao |
| 8,337,510 | B2 | 12/2012 | Rieber et al. |
| 8,343,031 | B2 | 1/2013 | Gertner |
| 8,348,827 | B2 | 1/2013 | Zwolinski |
| 8,388,630 | B2 | 3/2013 | Teague et al. |
| 8,409,112 | B2 | 4/2013 | Wynne et al. |
| 8,409,216 | B2 | 4/2013 | Parihar et al. |
| 8,409,217 | B2 | 4/2013 | Parihar et al. |
| 8,414,596 | B2 | 4/2013 | Parihar et al. |
| 8,419,749 | B2 | 4/2013 | Shelton, IV et al. |
| 8,425,533 | B2 | 4/2013 | Parihar et al. |
| 8,430,826 | B2 | 4/2013 | Uznanski et al. |
| 8,435,237 | B2 | 5/2013 | Bahney |
| 8,444,655 | B2 | 5/2013 | Parihar et al. |
| 8,579,914 | B2 | 11/2013 | Menn et al. |
| 8,585,712 | B2 | 11/2013 | O'Prey et al. |
| 8,591,521 | B2 | 11/2013 | Cherry et al. |
| 8,652,147 | B2 | 2/2014 | Hart |
| 8,672,206 | B2 | 3/2014 | Aranyi et al. |
| 8,696,683 | B2 | 4/2014 | LeVert |
| 8,721,658 | B2 | 5/2014 | Kahle et al. |
| 8,734,464 | B2 | 5/2014 | Grover et al. |
| 8,777,961 | B2 | 7/2014 | Cabrera et al. |
| 8,795,291 | B2 | 8/2014 | Davis et al. |
| 8,821,377 | B2 | 9/2014 | Collins |
| 8,827,968 | B2 | 9/2014 | Taylor et al. |
| 8,870,894 | B2 | 10/2014 | Taylor et al. |
| 8,906,035 | B2 | 12/2014 | Zwolinsk et al. |
| 8,906,036 | B2 | 12/2014 | Farascioni |
| 8,956,370 | B2 | 2/2015 | Taylor et al. |
| 8,968,329 | B2 | 3/2015 | Cabrera |
| 2002/0068943 | A1 | 6/2002 | Chu et al. |
| 2002/0082516 | A1 | 6/2002 | Stefanchik |
| 2003/0073970 | A1 | 4/2003 | Suga |
| 2003/0100909 | A1 | 5/2003 | Suzuki |
| 2003/0100919 | A1 | 5/2003 | Hopkins et al. |
| 2003/0199915 | A1 | 10/2003 | Shimm |
| 2003/0216773 | A1 | 11/2003 | Shimm |
| 2004/0097960 | A1 | 5/2004 | Terachi et al. |
| 2004/0138587 | A1 | 7/2004 | Lyons |
| 2005/0085808 | A1 | 4/2005 | Nakao |
| 2005/0165411 | A1 | 7/2005 | Orban |
| 2005/0236459 | A1 | 10/2005 | Gresham |
| 2005/0256425 | A1 | 11/2005 | Prusiner |
| 2005/0267492 | A1 | 12/2005 | Poncet et al. |
| 2006/0030750 | A1 | 2/2006 | Amer |
| 2006/0052799 | A1 | 3/2006 | Middleman et al. |
| 2006/0058776 | A1 | 3/2006 | Bilsbury |
| 2006/0169287 | A1 | 8/2006 | Harrison et al. |
| 2006/0200169 | A1 | 9/2006 | Sniffin |
| 2006/0200170 | A1 | 9/2006 | Aranyi |
| 2006/0229639 | A1 | 10/2006 | Whitfield |
| 2006/0229640 | A1 | 10/2006 | Whitfield |
| 2007/0016224 | A1 | 1/2007 | Nakao |
| 2007/0016225 | A1 | 1/2007 | Nakao |
| 2007/0073251 | A1 | 3/2007 | Zhou et al. |
| 2007/0088370 | A1 | 4/2007 | Kahle et al. |
| 2007/0135780 | A1 | 6/2007 | Pagedas |
| 2007/0135781 | A1 | 6/2007 | Hart |
| 2007/0186935 | A1 | 8/2007 | Wang et al. |
| 2007/0213743 | A1 | 9/2007 | McGuckin, Jr. |
| 2008/0188766 | A1 | 8/2008 | Gertner |
| 2008/0221587 | A1 | 9/2008 | Schwartz |
| 2008/0221588 | A1 | 9/2008 | Hollis et al. |
| 2008/0234696 | A1 | 9/2008 | Taylor et al. |
| 2008/0255597 | A1 | 10/2008 | Pravong et al. |
| 2008/0300621 | A1 | 12/2008 | Hopkins et al. |
| 2008/0312496 | A1 | 12/2008 | Zwolinski |
| 2009/0043315 | A1 | 2/2009 | Moon |
| 2009/0082779 | A1 | 3/2009 | Nakao |
| 2009/0182292 | A1 | 7/2009 | Egle et al. |
| 2009/0192510 | A1 | 7/2009 | Bahney |
| 2009/0240238 | A1 | 9/2009 | Grodrian et al. |
| 2010/0000471 | A1 | 1/2010 | Hibbard |
| 2010/0152746 | A1 | 6/2010 | Ceniccola et al. |
| 2011/0087235 | A1 | 4/2011 | Taylor et al. |
| 2011/0184311 | A1 | 7/2011 | Parihar et al. |
| 2011/0184434 | A1 | 7/2011 | Parihar et al. |
| 2011/0184435 | A1 | 7/2011 | Parihar et al. |
| 2011/0184436 | A1 | 7/2011 | Shelton, IV et al. |
| 2011/0190779 | A1 | 8/2011 | Gell et al. |
| 2011/0190781 | A1 | 8/2011 | Collier et al. |
| 2011/0190782 | A1 | 8/2011 | Fleming et al. |
| 2011/0264091 | A1 | 10/2011 | Koppleman et al. |
| 2011/0299799 | A1 | 12/2011 | Towe |
| 2012/0046667 | A1 | 2/2012 | Cherry et al. |
| 2012/0053406 | A1 * | 3/2012 | Conlon ............... A61B 17/29 600/109 |
| 2012/0083795 | A1 | 4/2012 | Fleming et al. |
| 2012/0083796 | A1 | 4/2012 | Grover et al. |
| 2012/0179165 | A1 * | 7/2012 | Grover ............... A61B 17/00 606/114 |
| 2012/0203241 | A1 | 8/2012 | Williamson, IV |
| 2013/0023895 | A1 | 1/2013 | Saleh |
| 2013/0103042 | A1 | 4/2013 | Davis |
| 2013/0116592 | A1 | 5/2013 | Whitfield |
| 2013/0184536 | A1 | 7/2013 | Shibley et al. |
| 2013/0190773 | A1 | 7/2013 | Carlson |
| 2013/0218170 | A1 | 8/2013 | Uznanski et al. |
| 2013/0245636 | A1 | 9/2013 | Jansen |
| 2013/0274758 | A1 | 10/2013 | Young et al. |
| 2013/0325025 | A1 | 12/2013 | Hathaway et al. |
| 2014/0046337 | A1 | 2/2014 | O'Prey et al. |
| 2014/0058403 | A1 | 2/2014 | Menn et al. |
| 2014/0180303 | A1 | 6/2014 | Duncan et al. |
| 2014/0222016 | A1 | 8/2014 | Grover et al. |
| 2014/0236110 | A1 | 8/2014 | Taylor et al. |
| 2014/0236167 | A1 * | 8/2014 | Shibley ............... A61J 1/10 606/114 |
| 2014/0243865 | A1 | 8/2014 | Swayze et al. |
| 2014/0249541 | A1 | 9/2014 | Kahle et al. |
| 2014/0276913 | A1 | 9/2014 | Tah et al. |
| 2014/0303640 | A1 | 10/2014 | Davis et al. |
| 2014/0309656 | A1 | 10/2014 | Gal et al. |
| 2014/0330285 | A1 | 11/2014 | Rosenblatt et al. |
| 2014/0350567 | A1 | 11/2014 | Schmitz et al. |
| 2014/0371759 | A1 | 12/2014 | Hartoumbekis |
| 2014/0371769 | A1 | 12/2014 | Menn |
| 2015/0018837 | A1 | 1/2015 | Sartor et al. |
| 2015/0045808 | A1 | 2/2015 | Farascioni |
| 2015/0305728 | A1 * | 10/2015 | Taylor ............... A61B 17/00234 606/114 |
| 2016/0022352 | A1 * | 1/2016 | Johnson ............... A61B 18/148 606/41 |
| 2016/0310134 | A1 | 10/2016 | Contini et al. |

(56) References Cited

U.S. PATENT DOCUMENTS

| | | |
|---|---|---|
| 2017/0049427 A1 | 2/2017 | Do et al. |
| 2017/0215904 A1 | 8/2017 | Wassef et al. |
| 2017/0224321 A1 | 8/2017 | Kessler et al. |
| 2017/0231611 A1* | 8/2017 | Holsten ............ A61B 17/00234 606/114 |
| 2017/0311964 A1 | 11/2017 | Desai et al. |
| 2017/0325798 A1 | 11/2017 | Prior |
| 2020/0305866 A1* | 10/2020 | Knapp ................. A61B 17/295 |
| 2021/0128129 A1* | 5/2021 | George ................. A61L 31/04 |

FOREIGN PATENT DOCUMENTS

| | | |
|---|---|---|
| DE | 8435489 U1 | 8/1986 |
| DE | 4204210 A1 | 8/1992 |
| DE | 19624826 A1 | 1/1998 |
| DE | 10327106 A1 | 12/2004 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| EP | 2583629 A2 | 4/2013 |
| ES | 2379920 A1 | 5/2012 |
| FR | 1272412 A | 9/1961 |
| GB | 246009 A | 1/1926 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004032760 A2 | 4/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |
| WO | 2011090866 A2 | 7/2011 |
| WO | 2013075103 A1 | 5/2013 |
| WO | 2014134285 A1 | 9/2014 |
| WO | 2015134888 A1 | 9/2015 |
| WO | 2015164591 A1 | 10/2015 |
| WO | 2017189442 A1 | 11/2017 |
| WO | 2018148744 A1 | 8/2018 |

OTHER PUBLICATIONS

European Search Report EP 12191639.9 dated Feb. 20, 2013.
European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report dated Feb. 12, 2019 issued in EP Application No. 18208634.
International Search Report issued in Appl. No. PCT/US2018/058609 dated Feb. 22, 2019.
Extended European Search Report issued in corresponding Appl. No. EP 19170619.1 dated Sep. 19, 2019 (8 pages).
Extended European Search Report issued in Appl. No. 19174966.2 dated Oct. 30, 2019 (10 pages).
Extended European Search Report issued in Appl. No. EP 19197987.1 dated Jan. 8, 2020 (10 pages).

* cited by examiner

SPECIMEN CAPTURE STAPLER

CROSS-REFERENCE TO RELATED APPLICATIONS

This application claims the benefit of and priority to U.S. Provisional Patent Application Ser. No. 62/824,106 filed Mar. 26, 2019, the entire disclosure of which is incorporated by reference herein.

TECHNICAL FIELD

The present disclosure relates generally to surgical apparatuses for use in minimally invasive surgical procedures, such as endoscopic and/or laparoscopic procedures, and more particularly, the present disclosure relates to a surgical apparatus including a specimen retrieval device for collecting body tissue(s) and/or body fluid(s) during these procedures.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized to pass through incisions and penetrate the abdominal wall, thereby permitting endoscopic surgery to be performed. Trocar tubes or cannula devices are extended into and left in place in the abdominal wall to provide access for endoscopic surgical tools. A camera or endoscope is inserted through a trocar tube to permit the visual inspection and magnification of a body cavity. The surgeon can then perform diagnostic and/or therapeutic procedures at the surgical site with the aid of specialized instrumentation, such as forceps, graspers, cutters, applicators, and the like, which are designed to fit through additional cannulas.

When removing certain tissues from the body cavity, for example tumor tissue, it is important that the tumor tissue does not come into contact with healthy or uninvolved tissue. If tumor tissue or tissue parts have to be removed, they may be introduced into an "extraction bag," also referred to herein as a "specimen bag," at the site where the tumor or diseased tissue has been detached from the surrounding tissue, after which the specimen bag is withdrawn from the body, thereby minimizing contact of the diseased tissue with healthy tissue.

Improved devices, including specimen bags for use in minimally invasive surgical procedures, remain desirable.

SUMMARY

The present disclosure provides surgical stapling devices and methods for using the devices. In embodiments, a surgical stapling device of the present disclosure includes an end effector including an anvil assembly and a cartridge assembly pivotally coupled to one another, the anvil assembly and the cartridge assembly being relatively movable such that the end effector is movable between an open position and a clamped position. The surgical stapling device of the present disclosure also includes a specimen bag including a body and a mouth defining an open end, the mouth attached to the anvil assembly and the cartridge assembly such that movement of the end effector to the open position moves the mouth of the specimen bag to an open position.

In some embodiments, the mouth of the specimen bag includes a drawstring housing having a drawstring therein.

Methods of the present disclosure include, in embodiments, advancing a surgical stapling device including an anvil assembly and a cartridge assembly into a body cavity adjacent tissue to be removed from a patient's body and placing the tissue to be removed from the patient's body into a specimen bag having a mouth attached to the anvil assembly and the cartridge assembly. The anvil assembly and the cartridge assembly are closed on the tissue and the surgical stapling device is fired to separate a tissue specimen from the tissue.

In some embodiments, the method of the present disclosure further includes grasping the tissue specimen to pull the tissue specimen deeper into the specimen bag.

In other embodiments, grasping the tissue specimen to pull the tissue specimen deeper into the specimen bag occurs after firing the surgical stapling device.

In embodiments, the method of the present disclosure further includes closing the mouth of the specimen bag after firing the surgical stapling device.

Closing the mouth of the specimen bag occurs, in embodiments, by proximally pulling a drawstring encompassing the mouth of the specimen bag.

In some embodiments, proximally pulling the drawstring encompassing the mouth of the specimen bag further includes detaching the mouth of the specimen bag from the anvil assembly and the cartridge assembly.

In other embodiments, proximally pulling the drawstring encompassing the mouth of the specimen bag further includes detaching the specimen bag from an adapter assembly of the surgical stapling device.

In yet other embodiments, proximally pulling the drawstring encompassing the mouth of the specimen bag includes removing the specimen bag from the patient's body.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
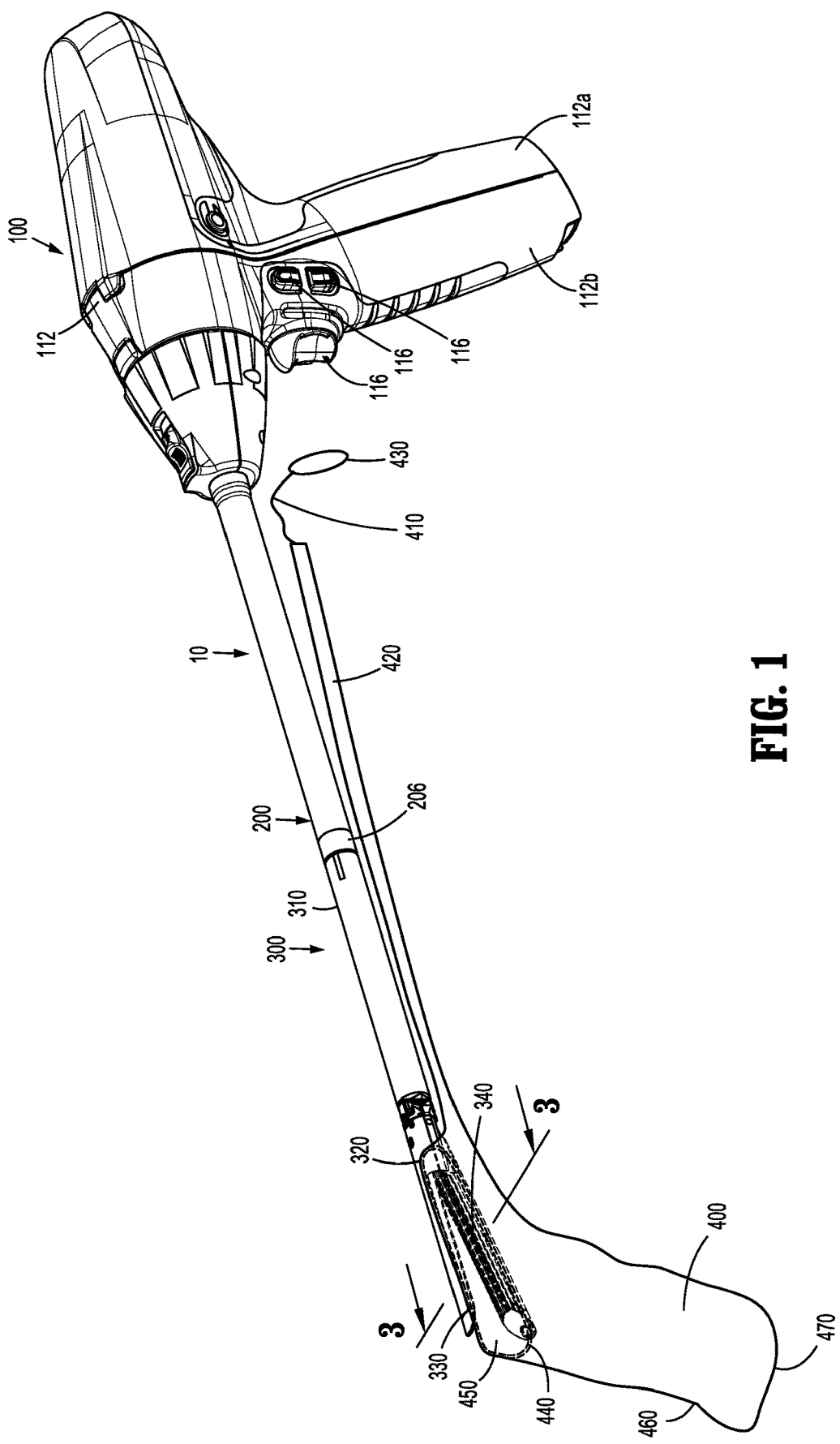
FIG. 1 is a perspective view of a surgical stapling device including a handle housing, an adapter assembly, an end effector, and a specimen bag attached thereto in accordance with an embodiment of the present disclosure.

The present disclosure provides a specimen retrieval device for use in minimally invasive surgical procedures. As used herein with reference to the present disclosure, minimally invasive surgical procedures encompass laparoscopic procedures, arthroscopic procedures, and endoscopic procedures, and refer to procedures utilizing scopes or similar devices having relatively narrow operating portions capable of insertion through a small incision in the skin.

The aspects of the present disclosure may be modified for use with various methods for retrieving tissue specimens during minimally invasive surgical procedures, sometimes referred to herein as minimally invasive procedures. Examples of minimally invasive procedures include, for example, cholecystectomies, appendectomies, nephrectomies, colectomies, splenectomies, and the like.

The presently disclosed specimen retrieval device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. The term "clinician" is used generally to refer to medical personnel including doctors, surgeons, nurses, and support personnel.

Turning now to FIG. 1, a surgical stapling device 10 in accordance with an embodiment of the present disclosure is in the form of a handheld surgical instrument. The surgical stapling device 10 includes a handle assembly 100, an adapter assembly 200, and an end effector 300. The handle assembly 100 is configured for selective connection with the adapter assembly 200 and, in turn, the adapter assembly 200 is configured for selective connection with the end effector 300.

The surgical stapling device 10 may be a manual surgical stapling device or a powered surgical stapling device. A powered device includes one or more motors and an internal or external power source, whereas the manual device has a movable handle and a mechanism for driving the functions of the apparatus. Examples of such stapling devices include those disclosed in U.S. Pat. Nos. 5,865,361; 5,782,396; 8,672,206; and International WO 04/032,760, the entire disclosures of each of which are incorporated by reference herein.

The handle assembly 100, the adapter assembly 200, and the end effector 300 will only further be described to the extent necessary to disclose aspects of the present disclosure. For a detailed description of the structure and function of exemplary handles, adapter assemblies, and end effectors, reference may be made to commonly owned U.S. Patent Appl. Pub. No. 2016/0310134, the entire disclosure of which is incorporated by reference herein.

With reference now to FIG. 1, the handle assembly 100 includes a housing shell 112, including a proximal half-section 112a and a distal half-section 112b. The housing shell 112 includes a plurality of actuators 116 (e.g., finger-actuated control buttons, knobs, toggles, slides, interfaces, and the like) for activating various functions of the surgical device 10 (FIG. 1). As noted above, the handle 112 may include a power source (not shown) configured to power and control various operations of the surgical device 10 or the handle 112. Alternatively, it is also envisioned that the handle 112 may be manually powered.

Figure 2:
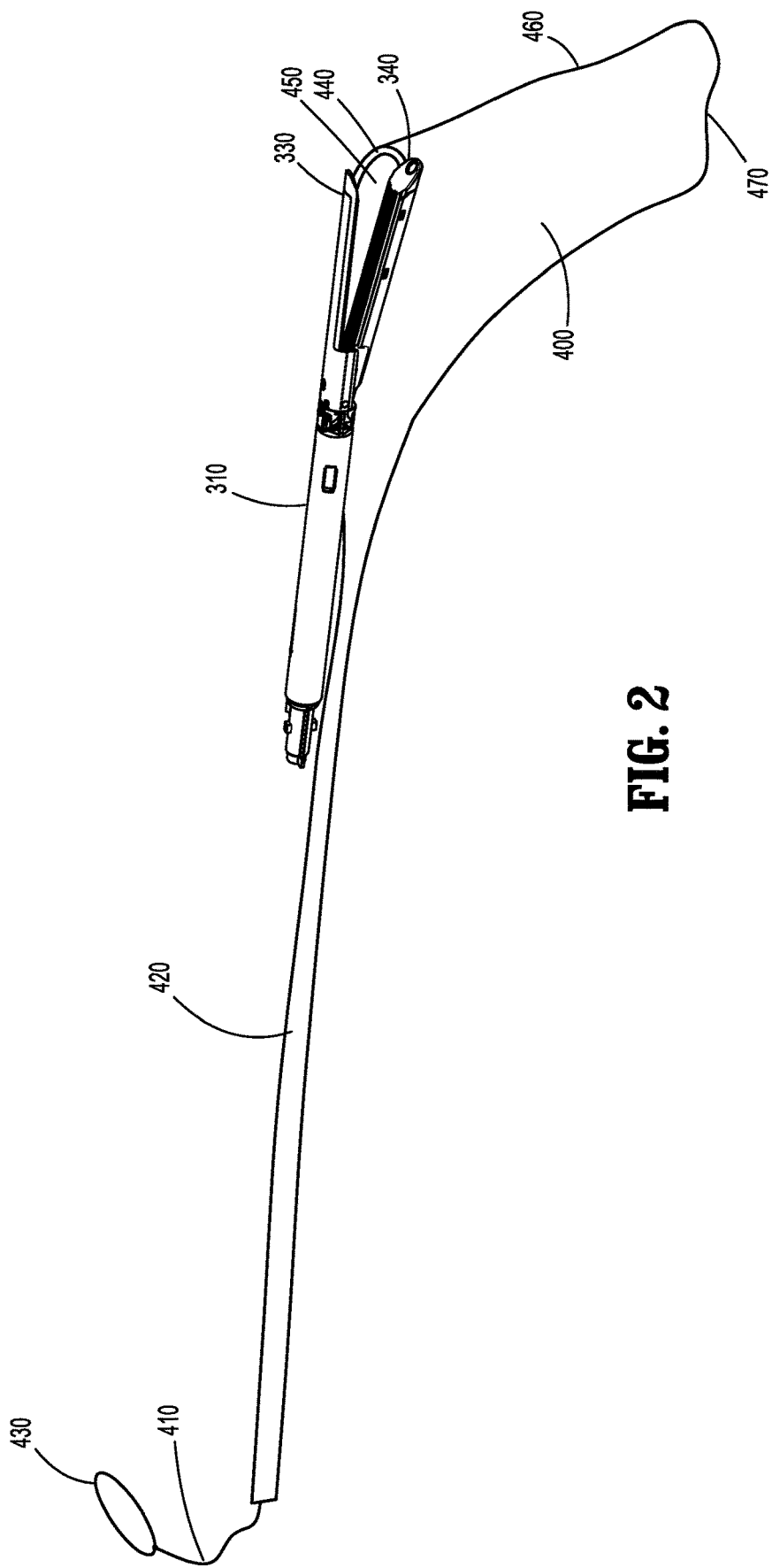
FIG. 2 is a perspective view, of the end effector and the specimen bag, including a drawstring and drawstring housing, of the surgical stapling device shown in FIG. 1.

Referring now to FIGS. 1-2, the end effector 300 is in the form of a single use loading unit. It should be understood, however, that other types of end effectors may also be used with the surgical device 10 of the present disclosure including, for example, end-to-end anastomosis loading units, multi-use loading units, transverse loading units, and curved loading units.

The end effector 300 includes a proximal body portion 310 and a tool assembly 320. The proximal body portion 310 of the end effector 300 is releasably attachable to the distal cap 206 of the adapter assembly 200 (FIG. 1) and the tool assembly 320 is pivotally attached to the proximal body portion 310 of the end effector 300. The tool assembly 320 of the end effector 300 includes an anvil assembly 330 and a cartridge assembly 340 pivotally coupled to one another such that the tool assembly 320 is movable between an open or unclamped position and a closed or clamped position.

Figure 3:
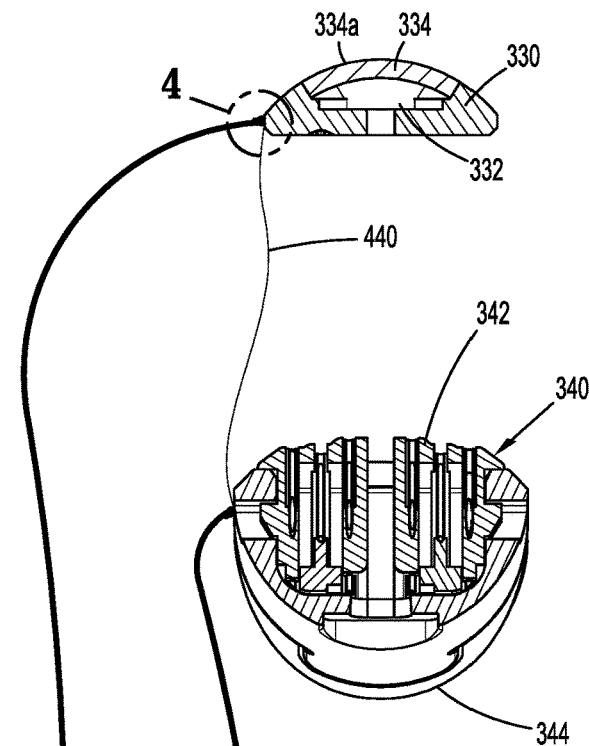
FIG. 3 is a cross-sectional view taken along section line 3-3 of FIG. 1.

As shown in FIG. 3, the anvil assembly 330 includes an anvil plate 332 and a cover plate 334 secured over the anvil plate 332 such that the cover plate 334 defines an outer surface 334a of the anvil assembly 330.

The cartridge assembly 340 includes a staple cartridge 342 and a cartridge carrier 344.

As depicted in FIGS. 1 and 2, the surgical stapling device 10 of the present disclosure also includes a specimen bag 400 adhered to both the anvil assembly 330 and the cartridge assembly 340 of the end effector 300. The specimen bag 400 includes a body 460 having a generally tubular or elongated configuration that is defined by an openable and closable portion (or mouth) 440 and a closed portion 470 (FIG. 1). The mouth 440 defines an opening 450 that opens when the anvil assembly 330 and the cartridge assembly 340 are in an open position. The specimen bag 400 includes a drawstring 410 within a drawstring housing 420. In embodiments the proximal portion of the drawstring 410 may possess a ring. 430 to facilitate grasping of the drawstring 410 (FIGS. 1 and 2). The drawstring housing 420 is adhered along the length of the adapter assembly 200. The specimen bag 400 may be compressed so that it fits between the anvil assembly 330 and the cartridge assembly 340 and can pass through a cannula, trocar, or similar device (not shown). The drawstring housing 420 will be long enough that it sticks outside of the trocar (not shown).

In other embodiments (not shown) the specimen bag 400 of the present disclosure may be attached to the anvil assembly 330, the cartridge assembly 340 of the end effector 300, or both, using loops that slide over the anvil assembly 330, the cartridge assembly 340 of the end effector 300, or both, to secure the specimen bag thereto. This would allow the specimen bag to be sold as a separate product for use with existing surgical stapling devices.

The body 460 of the specimen bag 400 may be made from any suitable biocompatible material (e.g., nylon, urethane, ripstop nylon or latex) capable of forming a flexible collapsible member, or membrane. In embodiments, the material from which the specimen bag is made is resilient, antistatic, pyrogen-free, non-toxic, and sterilizable. The specimen bag 400 may be opaque or clear. In some embodiments, the body 460 of the specimen bag 400 is formed of a nylon material, or combinations of nylon materials.

Figure 4:
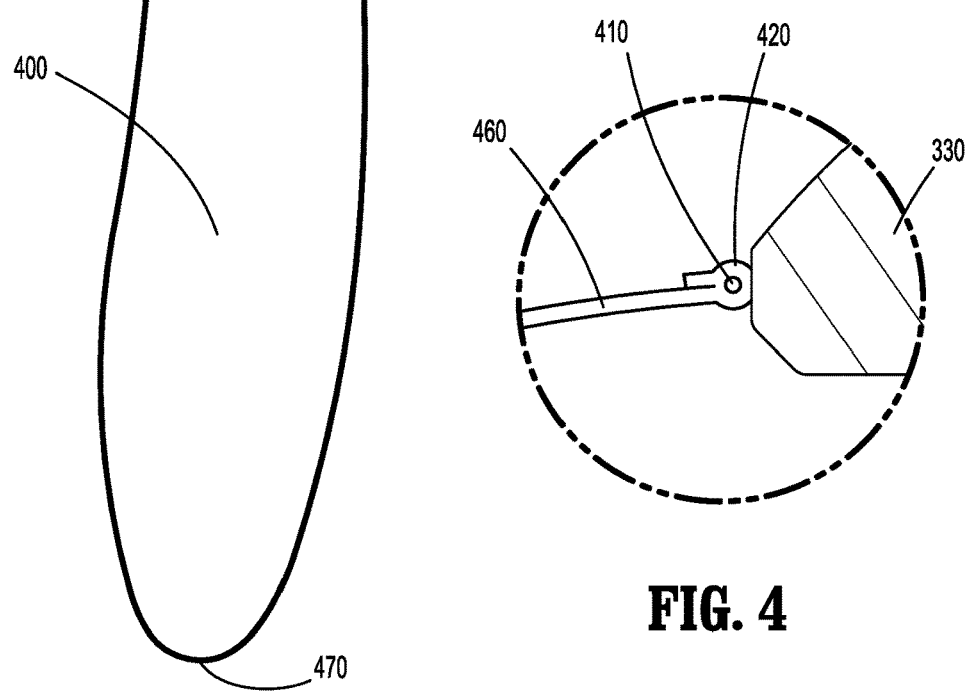
FIG. 4 is an enlarged view of the indicated area of detail shown in FIG. 3.

As shown in greater detail in FIGS. 3 and 4, in embodiments the specimen bag 400 is adhered to both the anvil assembly 330 and the cartridge assembly 340. As shown in FIG. 4, the drawstring housing 420, possessing the drawstring 410 therein, is attached to the anvil 330 and the cartridge assembly 340 using any suitable means, including biocompatible adhesives. Although not depicted, the drawstring 420 is similarly attached to the cartridge assembly.

Figure 5:
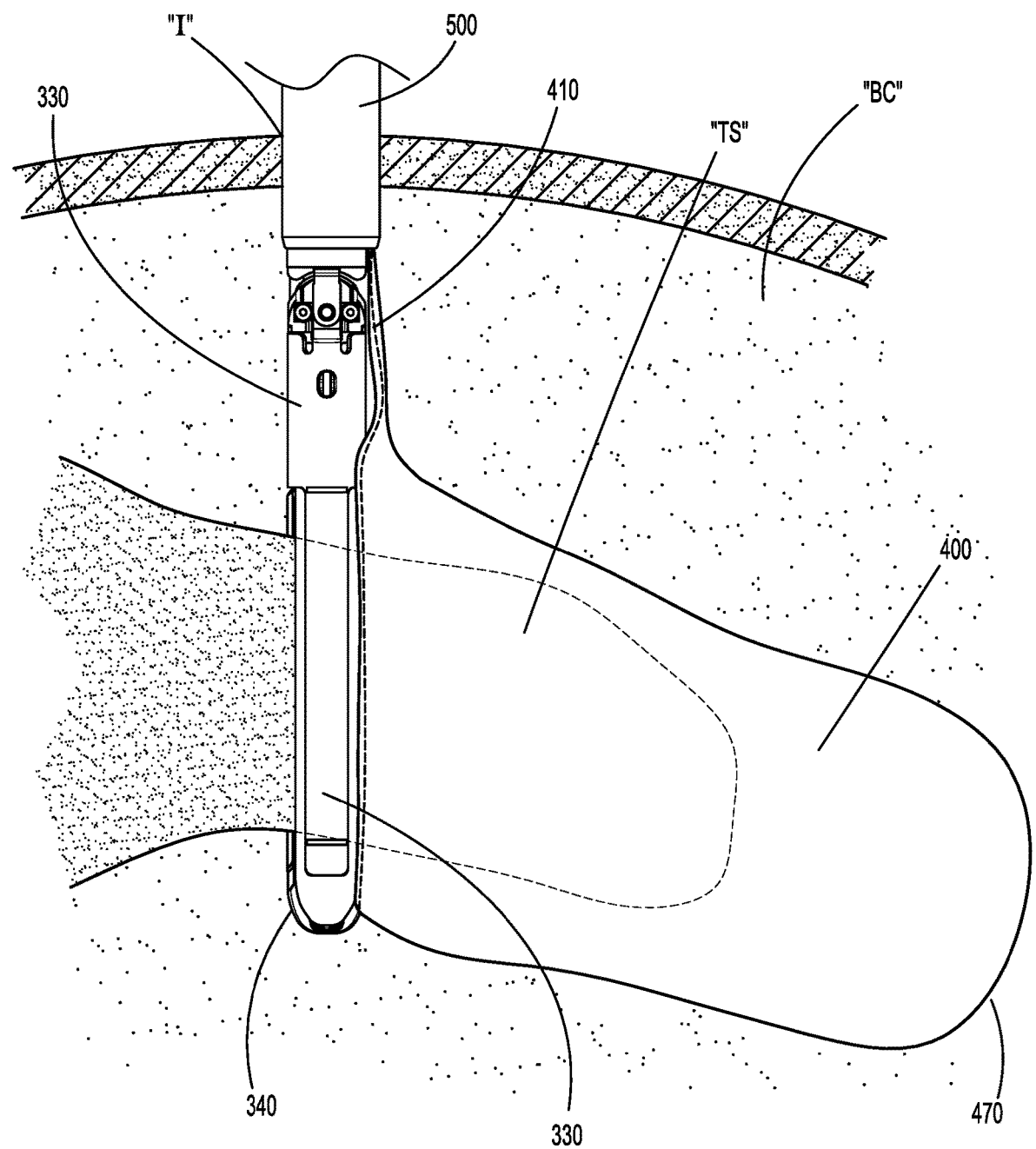
FIG. 5 is a top view of the distal portion of the surgical stapling device shown in FIG. 1 during a surgical procedure as the specimen bag is being deployed.

In use, as shown in FIG. 5, in embodiments a trocar 500 may be introduced through an incision "I" for access to a patient's body cavity "BC". The end effector 300 is inserted through the trocar 500 so that the anvil assembly 330 and the cartridge assembly 340 are positioned within the body cavity "BC". A tissue specimen "TS" is placed into the specimen bag 400 which will begin to unfold. The anvil assembly 330 and the cartridge assembly 340 are then closed on the tissue specimen "TS" and the surgical stapling device 10 is fired (not shown).

Figure 6:
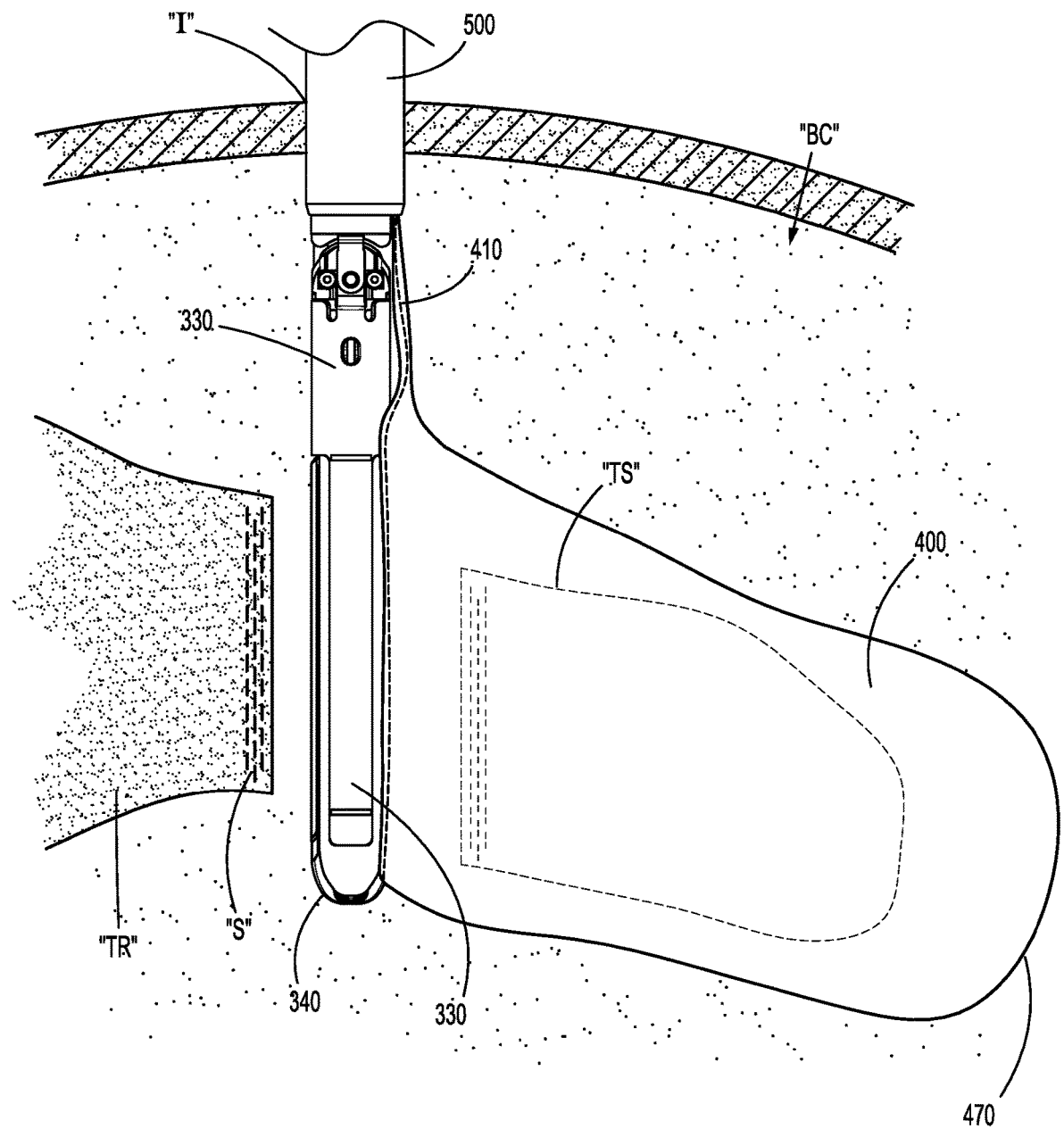
FIG. 6 is a top view of showing the specimen bag of the present disclosure after firing of the surgical stapling device shown in FIG. 5.

After firing the stapler, as shown in FIG. 6, the tissue specimen "TS" remains within the specimen bag 400, with the tissue remaining in the patient's body "TR" having a staple line "S" at the point of stapling.

Forceps may then be used to grasp the tissue specimen "TS" to pull the tissue specimen "TS" deeper into the specimen bag 400 (not shown).

Figure 7:
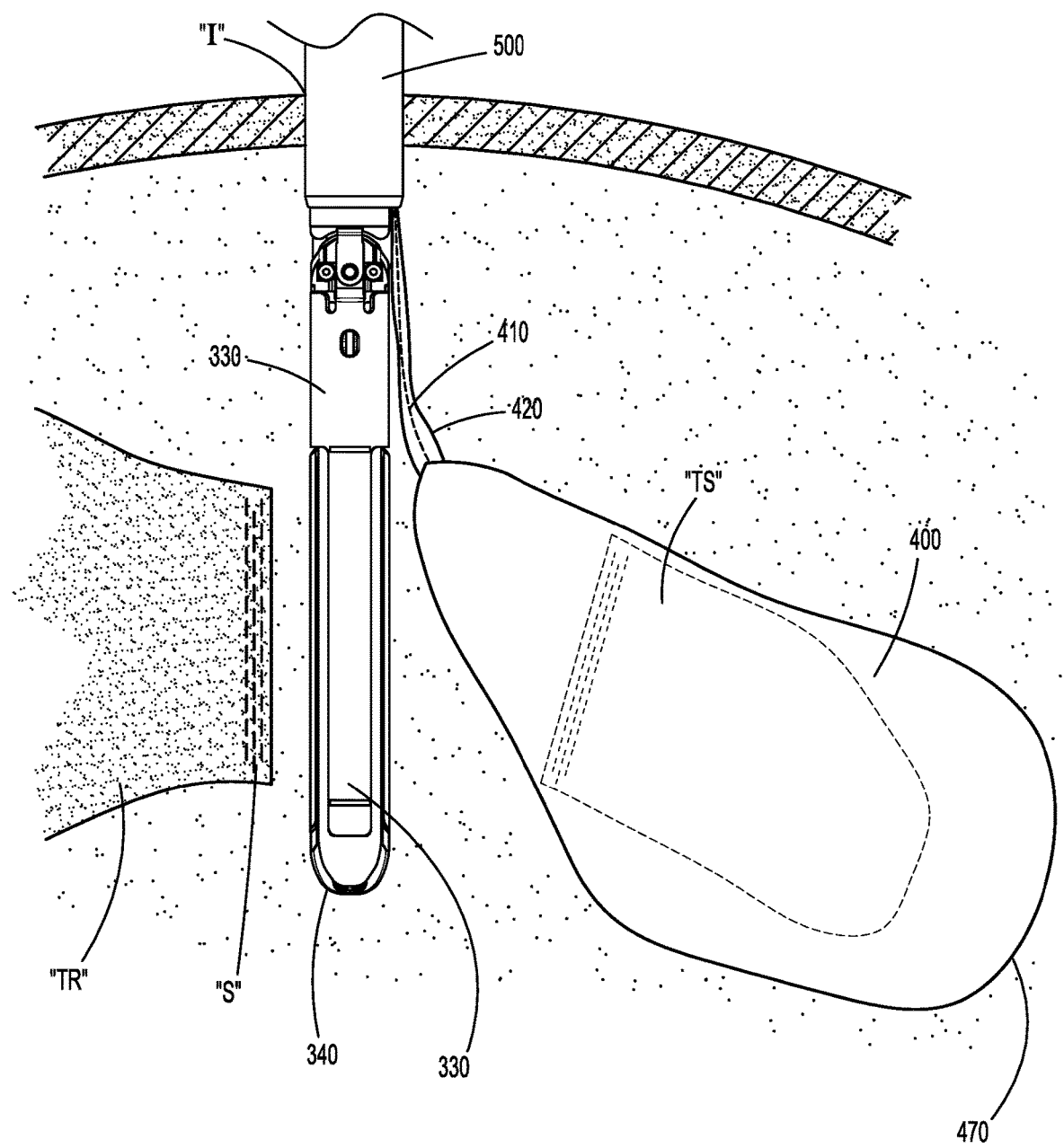
FIG. 7 is a top view showing the detachment of the specimen bag from the surgical stapling device shown in FIG. 6.

As shown in FIG. 7, once the tissue specimen "TS" is fully in the specimen bag 400, the drawstring 410 is pulled proximally (not shown) to close the specimen bag 400. While the specimen bag 400 is closing, the drawstring housing 420 detaches from the anvil assembly 330 and the cartridge assembly 340.

Figure 8:
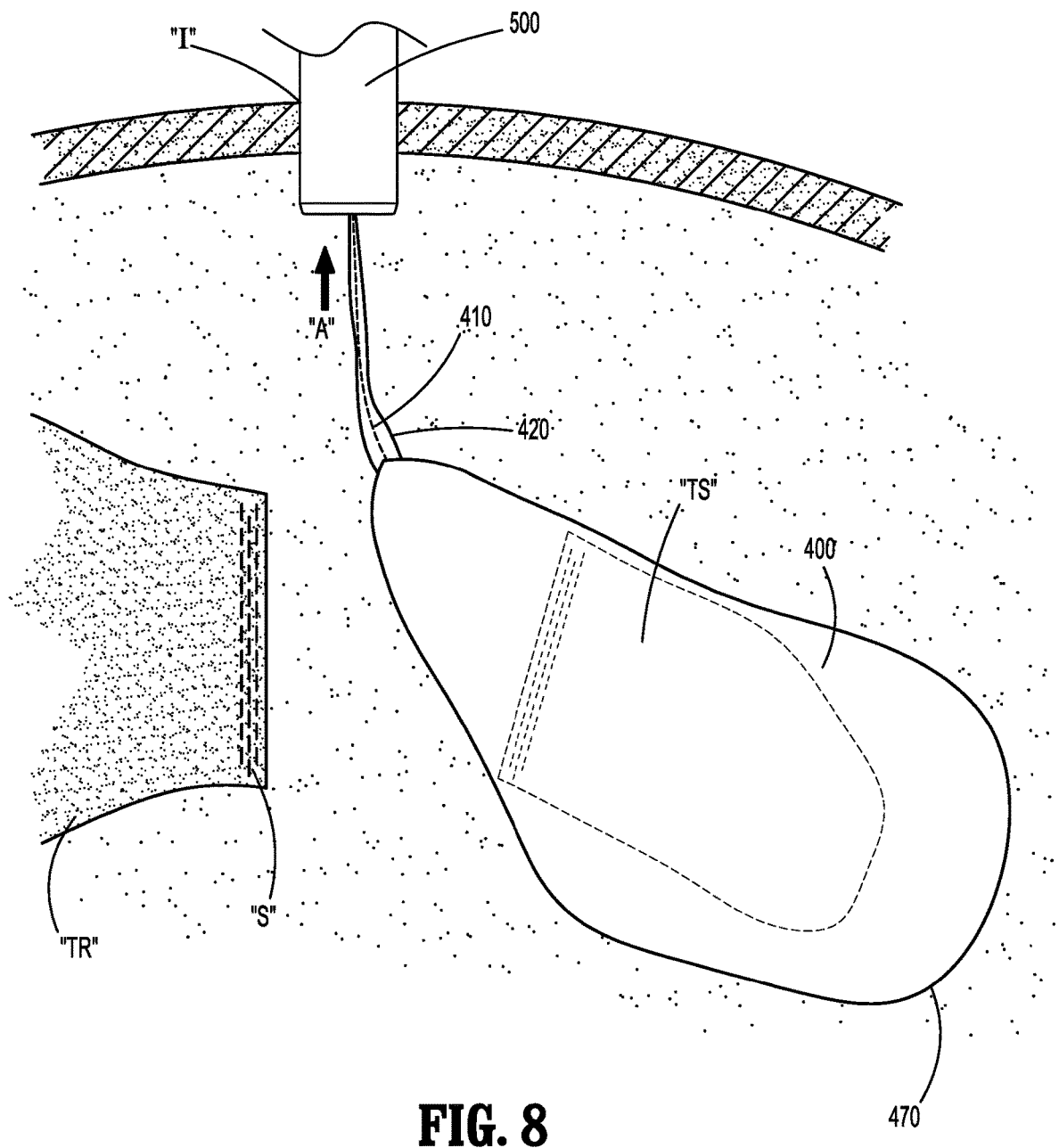
FIG. 8 is a side view showing removal of the drawstring and the drawstring housing from a patient's body after detachment of the specimen bag from the surgical stapling device shown in FIG. 7.

The drawstring housing 420 is then pulled to detach it from the adapter assembly 200 (not shown). At this point, the entire specimen bag 400 and drawstring housing 420 are completely detached from the surgical stapling device 10 and the surgical stapling device 10 can be removed from the patient (not shown). As shown in FIG. 8, the drawstring housing 420 with the drawstring 410 therein are then ready for removal through the trocar 300 by proximally pulling the drawstring housing 420 and the drawstring 410 therein (indicated by arrow "A" in FIG. 8). Next, the trocar 500 can be removed from the patient while the doctor ensures the specimen bag 400 remains closed by maintaining tension on the drawstring 410 (not shown), after which the specimen bag 400 can be removed from the patient (not shown).

Once the tissue specimen is removed from the patient, it will most likely be used for histopathological testing to ensure no cancer cells remain next to the cut line.

The devices and methods of the present disclosure provide several advantages over previous specimen retrieval devices.

For example, use of the devices of the present disclosure permits the direct placement of a diseased tissue specimen into a specimen bag to minimize the risk of spreading cancer cells during removal of the diseased tissue specimen from within a body cavity. It also reduces the maneuvering required with conventional devices to get the tissue specimen into the specimen bag, which can lead to the tissue specimen mistakenly coming in contact with healthy tissue.

In addition, the methods and devices of the present disclosure permit carrying out histopathology closer to the staple line, without having to worry about fluids being released from unhealthy tissue. With current practice, the best sample from the resected tissue is that portion closest to the cut line, to determine if any cancer daughter cells are left on the remaining healthy tissue. When the diseased tissue is cut, it is stapled as well. In some cases, the stapling deforms the tissue so that it can no longer be used for histopathology, therefore the pathologist must use the next closest sample of undamaged tissue, which is the width of three staples lines away from the cut line. However, if the resected tissue is not stapled, any contents inside the tissue could be expelled into its containing cavity. This could lead to an infection in the abdominal cavity. Using the devices and methods of the present disclosure, by immediately quarantining the resected tissue in a specimen bag, the risk of abdominal infection is less of a concern if the tissue being removed is not stapled or stapled with only one staple row far enough from the cut line to allow for histopathology.

Finally, less equipment is needed since the specimen bag and the stapling reload are combined.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the invention is not to be limited by what has been particularly shown and described, except as indicated by the appended claims.

What is claimed is:

1. A surgical stapling device, comprising:
   an end effector including an anvil assembly and a cartridge assembly pivotally coupled to one another, the anvil assembly and the cartridge assembly being relatively movable such that the end effector is movable between an open position and a clamped position; and
   a specimen bag including a body and a mouth defining an open end, the mouth attached to the anvil assembly and the cartridge assembly such that movement of the end effector to the open position moves the mouth of the specimen bag to an open position.

2. The surgical stapling device according to claim 1, wherein the mouth of the specimen bag includes a drawstring housing having a drawstring therein.

3. A method, comprising:
   advancing a surgical stapling device including an anvil assembly and a cartridge assembly into a body cavity adjacent tissue to be removed from a patient's body;
   placing the tissue to be removed from the patient's body into a specimen bag having a mouth attached to the anvil assembly and the cartridge assembly;
   closing the anvil assembly and the cartridge assembly on the tissue; and
   firing the surgical stapling device to separate a tissue specimen from the tissue.

4. The method of claim 3, further comprising grasping the tissue specimen to pull the tissue specimen deeper into the specimen bag.

5. The method of claim 4, wherein grasping the tissue specimen to pull the tissue specimen deeper into the specimen bag occurs after firing the surgical stapling device.

6. The method of claim 3, further comprising closing the mouth of the specimen bag after firing the surgical stapling device.

7. The method of claim 6, wherein closing the mouth of the specimen bag occurs by proximally pulling a drawstring encompassing the mouth of the specimen bag.

8. The method of claim 7, wherein proximally pulling the drawstring encompassing the mouth of the specimen bag further includes detaching the mouth of the specimen bag from the anvil assembly and the cartridge assembly.

9. The method of claim 8, wherein proximally pulling the drawstring encompassing the mouth of the specimen bag further includes detaching the specimen hag from an adapter assembly of the surgical stapling device.

10. The method of claim 8, wherein proximally pulling the drawstring encompassing the mouth of the specimen bag includes removing the specimen bag from the patient's body.

\* \* \* \* \*